(12) United States Patent
Arai et al.

(10) Patent No.: US 9,437,505 B2
(45) Date of Patent: Sep. 6, 2016

(54) METHOD OF MEASURING CONTAMINATION AMOUNT OF VAPOR PHASE GROWTH APPARATUS, AND METHOD OF MANUFACTURING EPITAXIAL WAFER

(71) Applicant: SHIN-ETSU HANDOTAI CO., LTD., Tokyo (JP)

(72) Inventors: Takeshi Arai, Fukushima (JP); Satoshi Inada, Fukushima (JP)

(73) Assignee: SHIN-ETSU HANDOTAI CO., LTD., Tokyo (JP)

(*) Notice: Subject to any disclaimer, the term of this patent is extended or adjusted under 35 U.S.C. 154(b) by 0 days.

(21) Appl. No.: 14/426,968

(22) PCT Filed: Sep. 26, 2013

(86) PCT No.: PCT/JP2013/076030
§ 371 (c)(1),
(2) Date: Mar. 9, 2015

(87) PCT Pub. No.: WO2014/061413
PCT Pub. Date: Apr. 24, 2014

(65) Prior Publication Data
US 2015/0243566 A1  Aug. 27, 2015

(30) Foreign Application Priority Data
Oct. 16, 2012 (JP) .................. 2012-229198

(51) Int. Cl.
*F27D 1/12* (2006.01)
*H01L 21/66* (2006.01)
(Continued)

(52) U.S. Cl.
CPC ........... *H01L 22/10* (2013.01); *C23C 16/4405* (2013.01); *C30B 25/16* (2013.01);
(Continued)

(58) Field of Classification Search
CPC ....... H01L 22/12; H01L 22/14; H01L 22/00; H01L 22/10; H01L 22/20; C23C 16/4405
See application file for complete search history.

(56) References Cited

U.S. PATENT DOCUMENTS 5,759,426 A   6/1998  Kobayashi et al.
2003/0073293 A1*  4/2003  Ferro .................. C23C 16/4405
                                                 438/478

(Continued)

FOREIGN PATENT DOCUMENTS

JP   03-101246 A   4/1991
JP   08-148552 A   6/1996

(Continued)

OTHER PUBLICATIONS

International Search Report of PCT/JP2013/076030 dated Dec. 17, 2013.

*Primary Examiner* — Zandra Smith
*Assistant Examiner* — Evan Clinton
(74) *Attorney, Agent, or Firm* — Arent Fox LLP (57) ABSTRACT

Carry out a vapor etching step of cleaning an inside of a chamber of a vapor phase growth apparatus by vapor etching using HCl gas (S1). Carry out an annealing step of sequentially annealing a predetermined number of silicon wafers, one by one, in a non-oxidizing atmosphere (S2, S3). Repeat the vapor etching step and the annealing step a prescribed number of times. After having carried out the vapor etching step and the annealing step the prescribed number of times (S4: Yes), collect contaminants on the surface of each of the wafers, and measure the Mo concentration using ICP-MS (S5). Evaluate the cleanliness of the vapor phase growth apparatus on the basis of each Mo concentration value and the relationship between the Mo concentrations (S6). Thus, provided is a method with which it is possible to measure, with high sensitivity, the contamination amount of a vapor phase growth apparatus.

13 Claims, 5 Drawing Sheets

(51) Int. Cl.
  *C23C 16/44* (2006.01)
  *C30B 25/16* (2006.01)
  *C30B 29/06* (2006.01)
  *G01N 33/00* (2006.01)
  *H01L 21/02* (2006.01)

(52) U.S. Cl.
  CPC ............ *C30B 29/06* (2013.01); *G01N 33/00* (2013.01); *G01N 33/0036* (2013.01); *H01L 21/02653* (2013.01); *H01L 22/12* (2013.01); *G01N 2033/0095* (2013.01); *H01L 21/0262* (2013.01); *H01L 21/02532* (2013.01)

(56) References Cited

U.S. PATENT DOCUMENTS

2005/0136657 A1\* 6/2005 Yokoi ................. C23C 16/4404
  438/680
2012/0077290 A1\* 3/2012 Wu .......................... G01N 1/32
  438/14

FOREIGN PATENT DOCUMENTS

JP  2006-228782 A  8/2006
JP  2010-040813 A  2/2010

\* cited by examiner

METHOD OF MEASURING CONTAMINATION AMOUNT OF VAPOR PHASE GROWTH APPARATUS, AND METHOD OF MANUFACTURING EPITAXIAL WAFER

CROSS-REFERENCE TO RELATED APPLICATIONS

This present application is a National Stage entry of International Application No. PCT/JP2013/076030, filed Sep. 26, 2013, which claims priority to Japanese Patent Application No. 2012-229198, filed Oct. 16, 2012. The disclosures of the prior applications are incorporated in their entirety reference.

FIELD OF THE INVENTION

This invention relates to a method of measuring the amount of contamination of a vapor phase growth apparatus, and a method of manufacturing an epitaxial wafer by using the method.

BACKGROUND OF THE INVENTION

In recent years, silicon epitaxial wafers manufactured by vapor-phase growing silicon films on silicon wafers have been used as substrates for imaging devices such as CCDs and CISs. In such epitaxial wafers for imaging devices, it is essential to reduce the level of a heavy-metal impurity in each wafer. This is because such a heavy-metal impurity existing in a wafer causes a defect called a white flaw (white spot).

In general, when an epitaxial wafer is manufactured, an epitaxial film is vapor-phase grown at a high temperature. Therefore, if a metal impurity is present in a chamber of a vapor phase growth apparatus when the epitaxial film is grown, the manufactured epitaxial wafer is contaminated by the metal impurity. As possible sources of such metal contamination, for example, a metal impurity attached to the vapor phase growth apparatus during maintenance (cleaning) thereof, a metal impurity contained in a material of the chamber, and a stainless steel component generally used for the apparatus and a piping system are conceivable in addition to a silicon crystal and a silicon-containing compound used as raw materials.

Heretofore, a method of evaluating cleanliness (degree of contamination) of a vapor phase growth apparatus has been known in which a metal impurity in an epitaxial wafer is measured, and cleanliness of a vapor phase growth apparatus in which the epitaxial wafer has been manufactured is evaluated based on the result of the measurement (refer to Patent Document 1, for example). In the method of Patent Document 1, a metal impurity in a silicon wafer is measured by a wafer lifetime (hereinafter sometimes abbreviated as WLT) method. As a typical example of the WLT method, a microwave photo conductivity decay (hereinafter abbreviated as a μ-PCD) method based on minority carrier lifetime has been known. In this method, for example, light is applied to a sample (substrate), and the lifetime of minority carriers caused by the light is detected based on change in reflectivity of a microwave, thereby to evaluate a metal impurity in the sample.

When a metal is taken into a wafer, the WLT value of the wafer is reduced. Therefore, metal contamination in an annealing furnace or a vapor phase growth apparatus can be managed by measuring and evaluating the WLT value of a wafer annealed in the annealing furnace or a wafer grown in the vapor phase growth apparatus. In other words, it is possible to determine whether an annealing furnace or a vapor phase growth apparatus, which is used in actual processing, is contaminated by a metal impurity, by preparing a wafer for contamination management, annealing the wafer in the annealing furnace or the vapor phase growth apparatus, and measuring the WLT value of the annealed wafer.

CITATION LIST

Patent Document

Patent Document 1: Japanese Laid-Open Patent Publication No. 2010-40813

SUMMARY OF INVENTION

Problems to be Solved by the Invention

By the way, regarding an epitaxial wafer for imaging devices such as CCDs or CISs, it is a challenge to increase the purity of the wafer in order to prevent occurrence of a white flaw. For this purpose, it is necessary to measure, with high sensitivity, the amount of contamination of a vapor phase growth apparatus. However, with recent increase in sensitivity of metal impurity measurement, it has become difficult to make accurate correspondence between a metal impurity and a white flaw by the conventional measuring method. That is, a situation occurs in which even though a difference in the amount of contamination due to a metal impurity measured by the WLT method or the like is small among a plurality of epitaxial wafers, a white flaw occurs in one wafer while no white flaw occurs in the other wafer. From this situation, it is conceivable that the conventional method cannot measure, with high sensitivity, the amount of contamination due to the metal impurity.

The invention is made in view of the above-described situation, and an object of the invention is to provide a method of measuring, with high sensitivity, the amount of contamination of a vapor phase growth apparatus, and a method of manufacturing a high-purity epitaxial wafer.

Solution to the Problems

In order to solve the above problems, according to the invention, a method of measuring an amount of contamination of a vapor phase growth apparatus includes: a vapor etching step of cleaning an inside of a chamber of a vapor phase growth apparatus by vapor etching using HCl gas; an annealing step of sequentially annealing a predetermined number of wafers, one by one, in a non-oxidizing atmosphere in the chamber after the vapor etching; and a measurement step of measuring a concentration of a metal impurity on a surface of each of the wafers annealed in the annealing step, as the amount of contamination of the vapor phase growth apparatus. The vapor etching step and the annealing step are repeatedly performed a predetermined number of times. The annealing step is performed such that the same wafers are used throughout the repeated annealing step and the order of the wafers to be annealed is not changed throughout the repeated annealing step. The measurement step is performed after the vapor etching step and the annealing step have been repeatedly performed the predetermined number of times.

According to the invention, in the vapor etching step, the inside of the chamber is subjected to the vapor etching using the HCl gas. Thereby, a reaction product of the HCl gas and a metal impurity existing in the vapor phase growth apparatus is generated, and a part of the reaction product remains in the chamber. After the vapor etching, the predetermined number of semiconductor wafers are introduced into the chamber one by one, and are sequentially annealed one by one in the non-oxidizing atmosphere (annealing step). Therefore, the surface of each wafer is contaminated by the metal impurity that is generated in the vapor etching step and remains in the chamber. Since the vapor etching step and the annealing step are repeatedly performed the predetermined number of times, contamination due to the metal impurity can be concentrated in a surface layer of the wafer. In the measurement step, the concentration of the metal impurity on the wafer surface, on which the vapor etching step and the annealing step have been repeatedly performed the predetermined number of times, is measured. Therefore, contamination of the vapor phase growth apparatus can be quantified, and measured with high sensitivity.

When the number of wafers to be annealed in the annealing step is plural, the annealing step is performed such that, throughout the repeated annealing step, the same wafers are used and the order of the wafers to be annealed is not changed. Therefore, the annealing order can be reflected in the amount of metal contamination at the surface of each wafer. Therefore, by observing the relationship among the metal impurity concentrations measured from the plurality of wafers, it is possible to easily determine, for example, the cause of the contamination of the vapor phase growth apparatus (whether the contamination is caused by cleaning using vapor etching or is caused by other factors than the cleaning).

The non-oxidizing atmosphere in the annealing step is preferably a hydrogen atmosphere. Since annealing in the non-oxidizing atmosphere is realized, an oxide film is prevented from being formed on the surface of the wafer during the annealing, and thereby the surface of the wafer is more likely to be contaminated with metal.

The number of wafers to be annealed in the annealing step is preferably three or more. Thereby, more information (decay of metal impurity concentration) can be obtained as compared with the case where the number of wafers is one or two, and therefore, it is possible to easily determine whether the cleanliness (degree of contamination) of the vapor phase growth apparatus is high or low, and the cause of contamination.

The number of times the vapor etching step and the annealing step are repeated is preferably four or more. It has been experimentally confirmed that, when the number of times of repetition is four or more, the metal impurity measuring sensitivity is particularly improved, and a difference in metal impurity concentration among the plurality of wafers is remarkable. Therefore, the number of times of repetition being four or more makes it easy to determine whether the cleanliness of the vapor phase growth apparatus is high or low, and the cause of contamination.

The annealing in the annealing step is preferably performed at 1000° C. to 1200° C. for 30 seconds or more. Thereby, the surface of each wafer can be favorably contaminated with metal.

In the measurement step, preferably, contamination on the wafer surface is collected, and the concentration of the metal impurity is measured by ICP-MS. Thereby, the concentration of the metal impurity can be obtained, and the contamination of the vapor phase growth apparatus can be quantified (the amount of the contamination can be measured). At this time, if the region from which the contamination is collected is the entire region of the wafer surface, the concentration of the metal impurity over the entire region can be obtained. On the other hand, if the region from which the contamination is collected is a part of the wafer surface, the concentration of the metal impurity in the part can be obtained. Therefore, an in-plane distribution of the concentration of the metal impurity can be obtained by measuring the concentrations in a plurality of different parts of the same wafer.

In the measurement step, a concentration of Mo is preferably measured as the concentration of the metal impurity. Mo has a low diffusion rate in a silicon wafer as the wafer. Therefore, by repeating the vapor etching step and the annealing step, Mo can be concentrated in the surface layer of the semiconductor wafer, whereby the Mo concentration can be measured with high sensitivity in the measurement step. In addition, as the wafer to be annealed, a silicon wafer is preferably used.

A method of manufacturing an epitaxial wafer according to the invention adopts the method of measuring an amount of contamination of a vapor phase growth apparatus according to the invention. In the method, an epitaxial film is vapor-phase grown on a wafer by using a vapor phase growth apparatus in which contamination caused by a metal impurity is reduced to or below a certain level, based on a result of measurement performed by the method of measuring an amount of contamination. According to this method, since the vapor phase growth apparatus is used in which metal contamination is reduced to or below a certain level by using the contamination amount measuring method of the invention which can measure the amount of contamination of a vapor phase growth apparatus with high sensitivity, a high-purity epitaxial wafer can be obtained.

DESCRIPTION OF EMBODIMENTS

Figure 1:
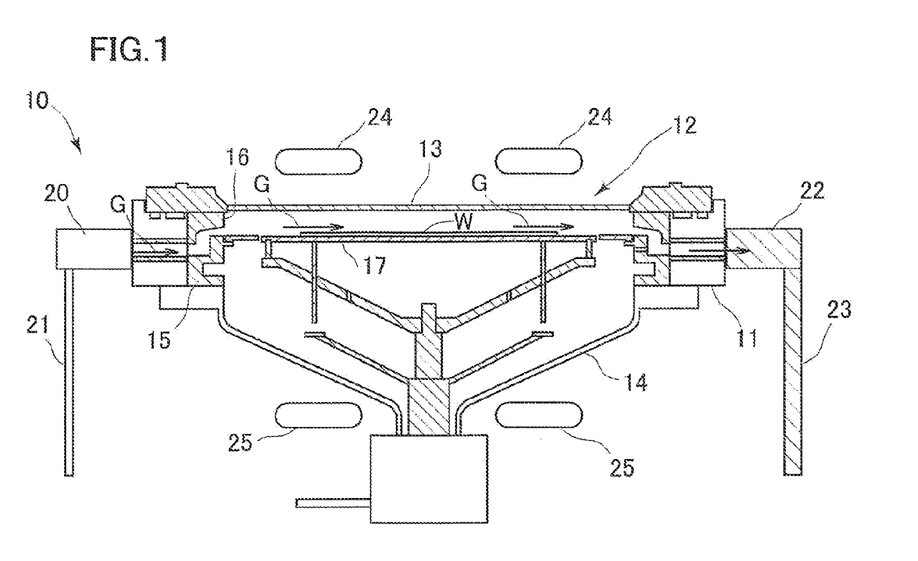
FIG. 1 is a lateral cross-sectional view of a vapor phase growth apparatus 10.

Hereinafter, embodiments of a method of measuring the amount of contamination of a vapor phase growth apparatus and a method of manufacturing an epitaxial wafer according to the invention will be described with reference to the drawings. FIG. 1 shows a lateral cross-sectional view of a single-wafer-processing-type vapor phase growth apparatus 10 as a preferable example of a vapor phase growth apparatus to be subjected to the contamination amount measuring method of the invention. The vapor phase growth apparatus 10 is a device for vapor-phase growing a silicon single crystal film on a front surface of a silicon wafer W (a device for manufacturing a silicon epitaxial wafer). The vapor phase growth apparatus 10 includes: a chamber base 11 made of SUS; transparent quartz members 13 and 14 that vertically sandwich the chamber base 11 to form a chamber 12 (reaction vessel); opaque quartz members 15 and 16 that are provided inside the chamber 12 and cover the chamber base 11 from the inside; and a susceptor 17 that horizontally supports the silicon wafer W.

The chamber 12 includes gas introduction tubes 20 and 21 through which a vapor-phase growth gas G containing a source gas (e.g., trichlorosilane) and a carrier gas (e.g., hydrogen) is introduced to a region above the susceptor 17 in the chamber 12 and is supplied onto a main front surface of the silicon wafer W on the susceptor 17. In addition, the chamber 12 includes gas exhaust tubes 22 and 23 provided on the side opposite to the side where the gas introduction tubes 20 and 21 are provided.

Further, heaters 24 and 25 that heat the silicon wafer W to an epitaxial growth temperature (e.g., 900 to 1200° C.) at the time of epitaxial growth are provided above and beneath the chamber 12. A plurality of the heaters 24 and 25 are provided in the horizontal direction. As the heaters 24 and 25, for example, halogen lamps may be used.

In the vapor phase growth apparatus 10, epitaxial wafers used as substrates for imaging devices such as CCDs or CISs are manufactured. As described above, with recent increase in sensitivity of metal impurity measurement, it has become difficult to make accurate correspondence between a metal impurity and a white flaw by the conventional measuring method (the WLT method or the like). The reason therefor may be that the conventional method cannot satisfactorily detect metals (Mo, Sn, W, Ta, Ti, Al, V and the like) that slowly diffuse in an epitaxial layer. Since a device such as an imaging device is significantly affected by metal impurities in an epitaxial layer, it is necessary to detect, with high sensitivity, such metal impurities that slowly diffuse in the epitaxial layer.

Since a reaction product (Si) accumulates in the chamber 12 as manufacturing of epitaxial wafers is repeated, the inside of the chamber 12 needs to be periodically subjected to vapor etching with HCl gas to remove the accumulated Si (subjected to cleaning). During the cleaning, a metal impurity may be generated from stainless or the like used as a material of the vapor phase growth apparatus 10. In the contamination amount measuring method of the invention, the cleaning by vapor etching is utilized for measurement of the amount of contamination of the vapor phase growth apparatus. Hereinafter, a method of evaluating cleanliness of the vapor phase growth apparatus 10, including the contamination amount measuring method of the invention, will be described.

Figure 2:
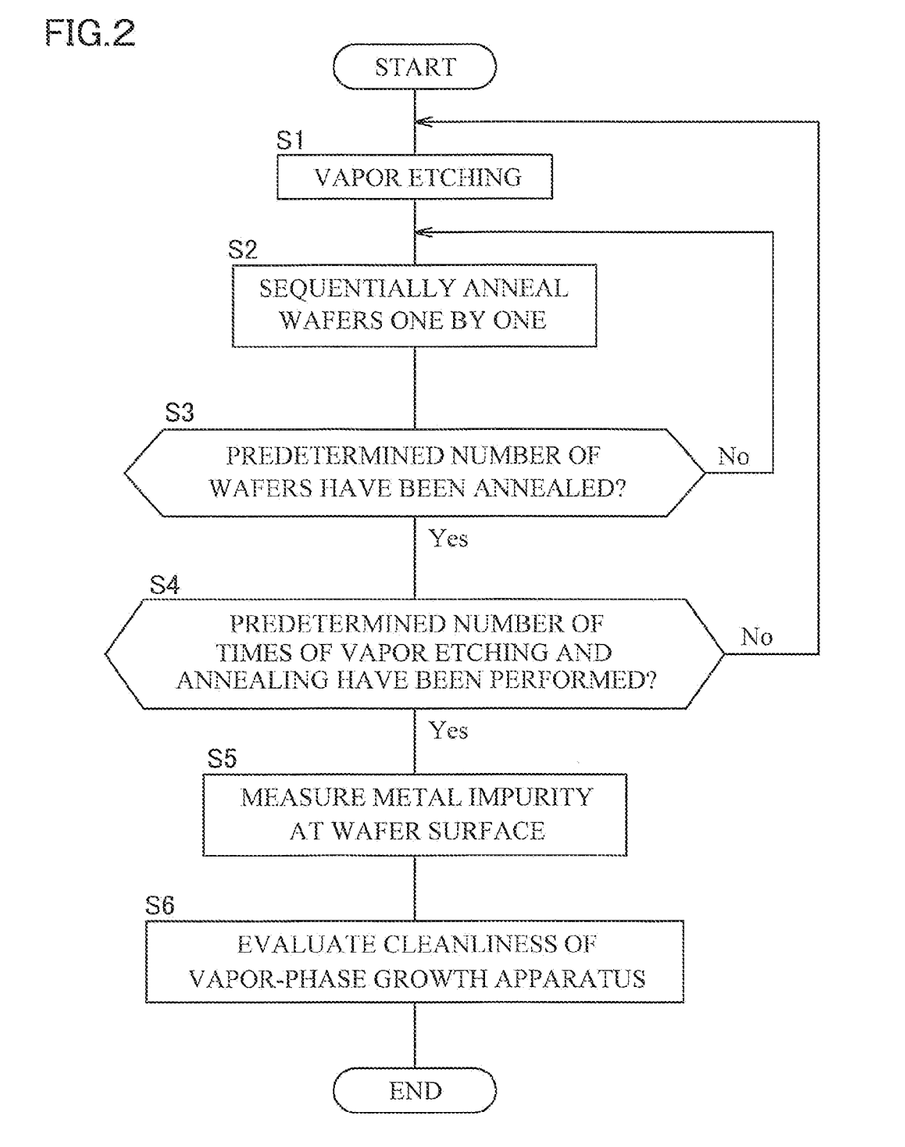
FIG. 2 is a flowchart of a cleanliness evaluation method for the vapor phase growth apparatus.

FIG. 2 is a flowchart showing the procedure of the method of evaluating cleanliness of the vapor phase growth apparatus 10. First, when manufacture of silicon epitaxial wafers has been repeated after maintenance of the vapor phase growth apparatus 10, cleaning is performed by vapor etching to remove Si accumulated in the chamber 12 (S1). Specifically, HCl gas is introduced into the chamber 12 through the gas introduction tubes 20 and 21, and the Si accumulated in the chamber 12 is removed with the HCl gas. The time of the vapor etching is set depending on the amount of the accumulated Si. At this time, due to the HCl gas, a metal impurity may be generated from a contamination causing portion (e.g., a corroded portion of a stainless member, or the like) of the vapor phase growth apparatus 10, or a reaction product of the HCl gas and a metal impurity attached to the inside of the vapor phase growth apparatus 10 (e.g., the gas introduction tubes 20 and 21, the inner wall of the chamber 12, or the like) may be generated. A part of the generated metal impurity or the generated reaction product of the HCl gas and the metal impurity (hereinafter simply referred to as "metal impurity") is discharged from the vapor phase growth apparatus 10 through the gas exhaust tubes 22 and 23, but the other part thereof remains in the chamber 12. When the vapor etching is performed, the silicon wafer is taken out of the chamber 12. The step S1 corresponds to "vapor etching step" of the invention.

Between the step S1 and the following step S2, an Si-based gas such as trichlorosilane may be introduced into the chamber 12 through the gas introduction tubes 20 and 21 so as to coat the inside of the chamber 12 (the inner wall of the chamber 12, the susceptor 17, and the like) with a thin Si film. By so doing, the inside of the chamber 12 is prevented from being contaminated by the metal impurity in the following step S2.

Then, a predetermined number of silicon wafers are prepared, and the prepared silicon wafers are sequentially annealed one by one in the chamber 12 (on the susceptor 17) (S2). Specifically, first, the first silicon wafer is put on the susceptor 17 and annealed. After the annealing, the silicon wafer is taken out of the chamber 12. Until the number of annealed silicon wafers reaches a predetermined number (S3: No), the second to the last (corresponding to the predetermined number) silicon wafers are sequentially annealed in the same manner as that for the first silicon wafer (S2). At this time, hydrogen is introduced into the chamber 12 through the gas introduction tubes 20 and 21 so that the annealing is performed in a hydrogen atmosphere. Thereby, an oxide film is prevented from being formed on the surface of the silicon wafer, and the surface of the silicon wafer is contaminated with the metal impurity. During the annealing, the temperature inside the chamber 12 is preferably 1000° C. to 1200° C., and the annealing time is preferably 30 seconds or more.

The number of silicon wafers to be annealed is not particularly limited (may be one), but preferably is three or more. The number of silicon wafers to be annealed being three or more makes it easy to understand regularity among the Mo concentrations of the silicon wafers, which are measured in later-described step S5, and thereby makes it easy to determine whether cleanliness of the vapor phase growth apparatus 10 is high or low, and the cause of contamination. The step S2 corresponds to "annealing step" of the invention.

The step S1 (vapor etching step) and the step S2 (annealing step) are repeatedly performed a predetermined number of times. That is, when the predetermined number of silicon wafers have been annealed (S3: Yes), it is determined whether the number of times of repetition of the steps S1 and S2 has reached the predetermined number of times (S4). If the number of times of repetition has not yet reached the predetermined number of times (S4: No), the process returns back to the step S1, and the inside of the chamber 12 is again subjected to vapor etching with the HCl gas. Since the Si accumulated in the chamber 12 has been removed by the first vapor etching, the second and subsequent vapor etching steps are performed for capturing the metal impurity that has not been completely captured by the first vapor etching, rather than for removing the accumulated Si.

The annealing step S2 is also repeatedly performed the predetermined number of times. Throughout the repeated step, the same silicon wafers are used, and the order of the silicon wafers to be annealed is not changed. That is, for example, when three silicon wafers W1, W2 and W3 are annealed in this order in the first annealing step, the same silicon wafers W1, W2 and W3 are used in the second and subsequent annealing steps. The silicon wafer W1 is annealed first, the silicon wafer W2 is annealed second, and the silicon wafer W3 is annealed third.

As described above, by repeatedly performing the steps S1 and S2 the predetermined number of times, the metal impurity whose diffusion rate in the silicon wafer is low can be concentrated in a surface layer of the silicon wafer. When a plurality of silicon wafers are annealed, the order of the silicon wafers to be annealed is not changed throughout the repeated annealing step, whereby the annealing order can be reflected in the amount of metal contamination of each silicon wafer. For example, if a large amount of metal impurity is generated in the chamber 12 due to the step S1 (cleaning), it is conceivable that the amount of metal contamination of the silicon wafer to be annealed first will be largest.

The number of times the steps S1 and S2 are repeated maybe any number of times as long as the amount of metal contamination can be measured with high sensitivity in the later-described step S5, but preferably is four or more. It has experimentally been confirmed that the number of times of repetition being four provides a remarkable difference in the amount of metal contamination among the plurality of silicon wafers. This experimental result will be described later.

When the steps S1 and S2 have been performed the predetermined number of times (S4: Yes), the concentration of the metal impurity on the surface of each annealed silicon wafer W is measured (S5). In this step S5, for example, Mo concentration is measured as the concentration of the metal impurity. Mo has a low diffusion rate in Si, and Mo is often included in the material of the vapor phase growth apparatus 10. Therefore, a larger amount of Mo is included in the surface layer of the annealed silicon wafer as compared with other metal impurities, and it is conceivable that the Mo concentration reflects the actual cleanliness (the amount of metal contamination) of the vapor phase growth apparatus 10.

Specifically, in the step S5, for example, WSA (Wafer Surface Analysis) is performed in which a chemical solution such as HF is dropped on the wafer surface and the droplets are caused to sweep the wafer surface (caused to roll on the wafer surface), thereby collecting contamination on the wafer surface together with the droplets. The collected droplets are subjected to ICP-MS (Inductively Coupled Plasma Mass Spectrometry) to measure the concentration of Mo included in the droplets. When the rolling range of the chemical solution is the entire range of the wafer surface (entire surface), the Mo concentration over the entire wafer surface (an average of Mo concentrations in different parts) is obtained. On the other hand, when the rolling range of the chemical solution is a part of the wafer, the Mo concentration in the part is obtained. The step S5 corresponds to "measuring step" of the invention.

Since the Mo concentrations of the wafers measured in the step S5 correspond to the amount of contamination of the vapor phase growth apparatus 10, the cleanliness of the vapor phase growth apparatus 10 is evaluated based on the Mo concentrations (S6). When the number of silicon wafers annealed in the step S2 is only one, it is determined whether the cleanliness of the vapor phase growth apparatus 10 is high or low, based on, for example, whether the Mo concentration of the wafer exceeds a predetermined threshold. When three or more silicon wafers have been annealed, it is determined that the cleanliness is low if the maximum Mo concentration among the Mo concentrations of the respective silicon wafers exceeds a predetermined threshold, and it is determined that the cleanliness is high if all the Mo concentrations are lower than the threshold. Further, simultaneously with the evaluation as to whether the cleanliness is high or low, it is determined whether metal contamination is caused by the step S1 (cleaning), based on the relationship among the levels of the Mo concentrations of the respective silicon wafers. Specifically, if there is a tendency that the silicon wafer which is earlier in the order of annealing has the higher Mo concentration, it is determined that the metal contamination of the silicon wafer is mainly caused by the cleaning (step S1). In this case, on assumption that the cause of contamination is in the region subjected to the cleaning (the region exposed to the HCl gas) in the vapor phase growth apparatus 10, the region is cleaned or replaced, thereby enhancing the cleanliness of the vapor phase growth apparatus 10. If no difference is observed in the Mo concentrations of the respective silicon wafers, it is determined that the metal contamination of the silicon wafer is mainly caused by a factor other than the cleaning. In this case, on assumption that the cause of contamination is in the region not subjected to the cleaning (the region not exposed to the HCl gas) in the vapor phase growth apparatus 10, the region is cleaned or replaced, thereby enhancing the cleanliness of the vapor phase growth apparatus 10.

The method of evaluating a vapor phase growth apparatus according to the present embodiment has been described above. As described above, according to the evaluation method of the present embodiment, since the vapor etching and the annealing are repeatedly performed a predetermined number of times, Mo as a metal impurity can be concentrated in the surface layer of the silicon wafer. Therefore, Mo whose diffusion rate in Si is low can be measured with high sensitivity. Further, the cause of contamination can be easily determined by observing the relationship in Mo concentration among the plurality of silicon wafers. For example, by using the vapor phase growth apparatus 10 which is managed so that the Mo concentration measured in the step S5 is equal to or lower than a certain level, it is possible to obtain a high-purity silicon epitaxial wafer with less metal impurity.

The procedure of the vapor phase growth is as follows. First, a silicon wafer W is put into the chamber 12 adjusted to a wafer throw-in temperature (e.g., 650° C.), and set on the susceptor 17 with the surface of the wafer facing upward. Since before the silicon wafer W is put into the chamber 12, hydrogen gas has been introduced into the chamber 12 through the gas introduction tubes 20 and 21 and a purge gas introduction tube.

Next, the silicon wafer W on the susceptor 17 is heated to a hydrogen annealing temperature (e.g., 1050 to 1200° C.) by the heaters 24 and 25. Next, vapor etching is performed to remove a natural oxide film formed at the surface of the silicon wafer W. Specifically, this vapor etching is performed until just before vapor-phase growth as a next step.

Next, the silicon wafer W is cooled down to a desired growth temperature (e.g., 1050 to 1180° C.) Then, a source gas (e.g., trichlorosilane) and a purge gas (e.g., hydrogen) are supplied to the surface of the silicon wafer W substantially horizontally through the gas introduction tubes 20 and 21 and the purge gas introduction tube, respectively, whereby a silicon single crystal film is vapor-phase grown on the surface of the silicon wafer W, and thus a silicon epitaxial wafer is manufactured. Finally, the silicon epitaxial wafer is cooled down to a wafer takeout temperature (e.g., 650° C.), and taken out of the chamber 12.

EXAMPLES

Hereinafter, the invention will be specifically described by means of examples and a comparative example. However, the invention is not limited by the examples and the comparative example.

Example 1

After maintenance of a vapor phase growth apparatus, when about 1000 silicon epitaxial wafers having a diameter of 300 mm had been manufactured, a chamber was subjected to vapor etching (VE) using HCl gas, and immediately thereafter, a silicon wafer was put in the chamber and annealed in H2 atmosphere at 1130° C. for 60 seconds. After the wafer was taken out, a second wafer was put in the chamber, subjected to the same annealing as above, and taken out. Further, a third wafer was put in the chamber, subjected to the same annealing as above, and taken out. Then, contamination at the surface of each wafer was collected, and the Mo concentration was measured by ICP-MS. Subsequently, the same VE as above was performed. Thereafter, the same three wafers as above were sequentially put in the chamber in the same order as above, and subjected to the same annealing as above. The vapor etching step and the annealing step were repeated up to four times in total. After the second and the fourth annealing had been completed, the Mo concentration was measured by ICP-MS in the same manner as that at the completion of the first annealing.

Figure 3:
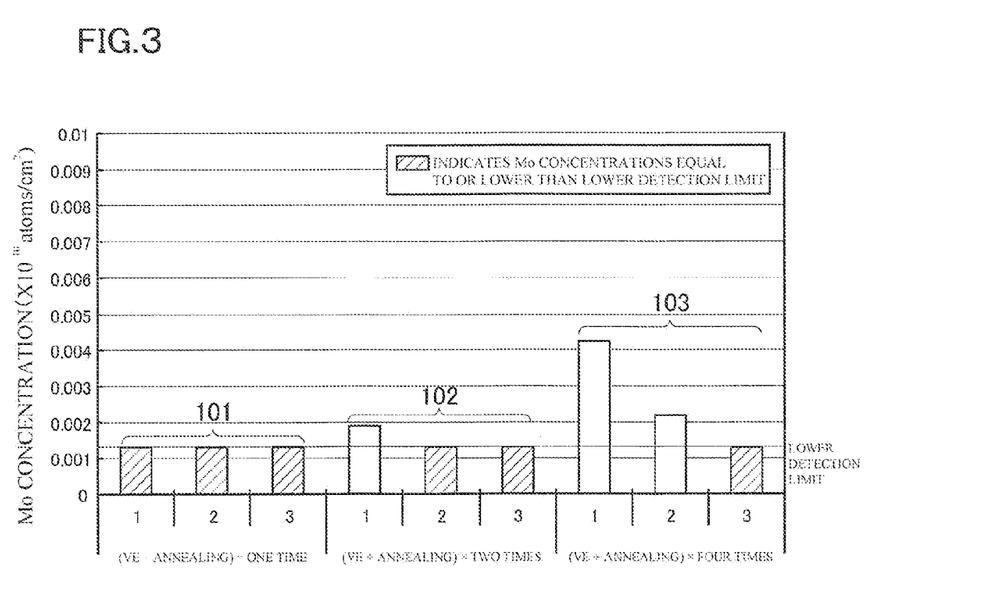
FIG. 3 is a diagram showing the dependence of Mo concentration on the number of wafers and the dependence of Mo concentration on the number of times of VE and annealing, as a result of measurement according to Example 1.

The result of the measurement is shown in FIG. 3. A group 101 on the left side in FIG. 3 represents the measurement result obtained when the VE and the annealing were performed only one time, a group 102 in the center represents the measurement result obtained when the VE and the annealing were repeated two times, and a group 103 on the right side represents the measurement result obtained when the VE and the annealing were repeated four times. The number "1" in the horizontal axis indicates the result of the first wafer (firstly annealed wafer), "2" indicates the result of the second wafer (secondly annealed wafer), and "3" indicates the result of the third wafer (thirdly annealed wafer). As shown in FIG. 3, in the group 101, the Mo concentrations of all the wafers are equal to or lower than a lower detection limit. However, in the group 102, the Mo concentration of the first wafer is a measurable value. Further, the Mo concentration of the first wafer in the group 103 is significantly larger than that in the group 102, and the Mo concentration of the second wafer is larger than the lower detection limit. That is, the measurement result indicates that the Mo concentrations were measured with high sensitivity by repeating the VE and the annealing four times.

In the group 103, the following relationship is obtained: Mo concentration of the first wafer>Mo concentration of the second wafer>Mo concentration of the third wafer. That is, the first wafer that is most affected by the VE has the highest Mo concentration. Thus, it is conceivable that the vapor phase growth apparatus used this time is likely to be affected by metal contamination due to the cleaning by the VE.

Figure 4:
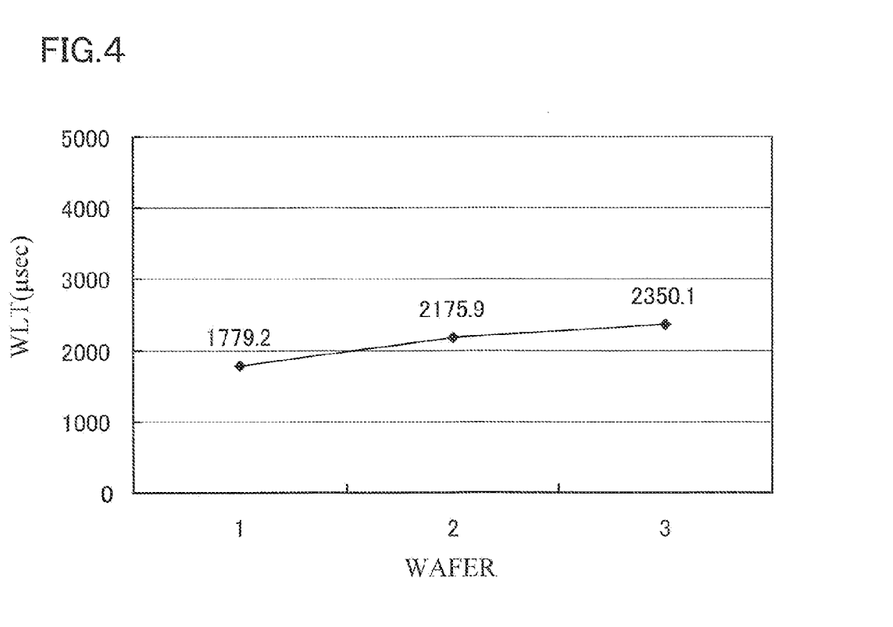
FIG. 4 is a diagram showing WLTs of three wafers when VE and annealing are performed four times, as a result of measurement according to a comparative example of Example 1.

As a comparative example, three wafers were subjected to four times of the VE and the annealing, and the wafer lifetime (WLT) of each wafer was measured. The conditions of the VE and the annealing were the same as those of Example 1. The result of the measurement is shown in FIG. 4. In FIG. 4, the number "1" in the horizontal axis indicates the result of the first wafer, "2" indicates the result of the second wafer, and "3" indicates the result of the third wafer. In addition, a numerical value above each plot point in FIG. 4 is the value of WLT. As shown in FIG. 4, the WLTs are slightly reduced in order of the third wafer, the second wafer, and the first wafer, but the differences are negligible, which makes it difficult to determine the cause of contamination.

Example 2

Figure 5:
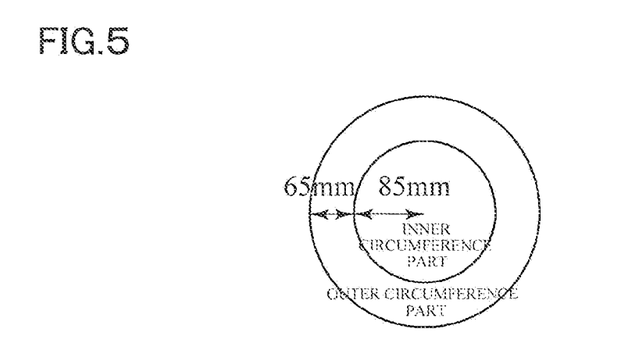
FIG. 5 is a diagram schematically showing an inner circumference part and an outer circumference part of a wafer having a diameter of 300 mm.
Figure 6:
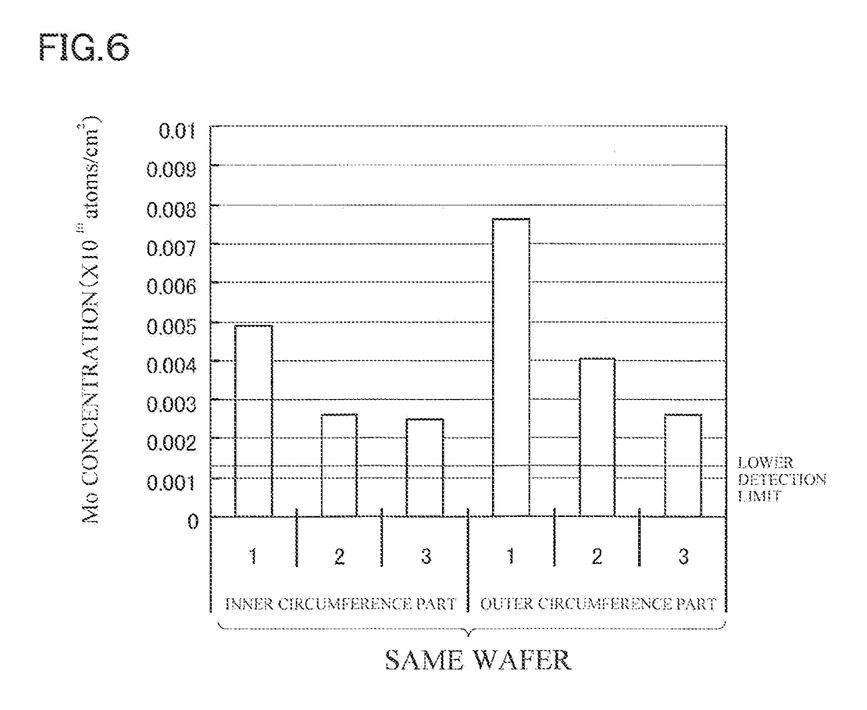
FIG. 6 is a diagram showing Mo concentrations measured when a droplet rolling range of WSA is the inner circumference part and the outer circumference part, respectively, as a result of measurement according to Example 2.

An experiment similar to Example 1 was conducted. However, in Example 2, a part within a radius of 85 mm of a silicon epitaxial wafer having a diameter of 300 mm was regarded as an inner circumference part (refer to FIG. 5), and a part corresponding to 65 mm from the radius of 85 mm to 150 mm (outermost periphery) of the silicon epitaxial wafer was regarded as an outer circumference part (refer to FIG. 5). The number of repetition of VE and annealing was four. The inner circumference part and the outer circumference part of each of three wafers were compared for the Mo concentration. FIG. 6 shows the result of the measurement. As shown in FIG. 6, in each of the first, second, and third wafers, the Mo concentration of the outer circumference part is higher than the Mo concentration of the inner circumference part. The outer circumference part is usually more contaminated than the inner circumference part, and the same result as usual is achieved.

Example 3

Figure 7:
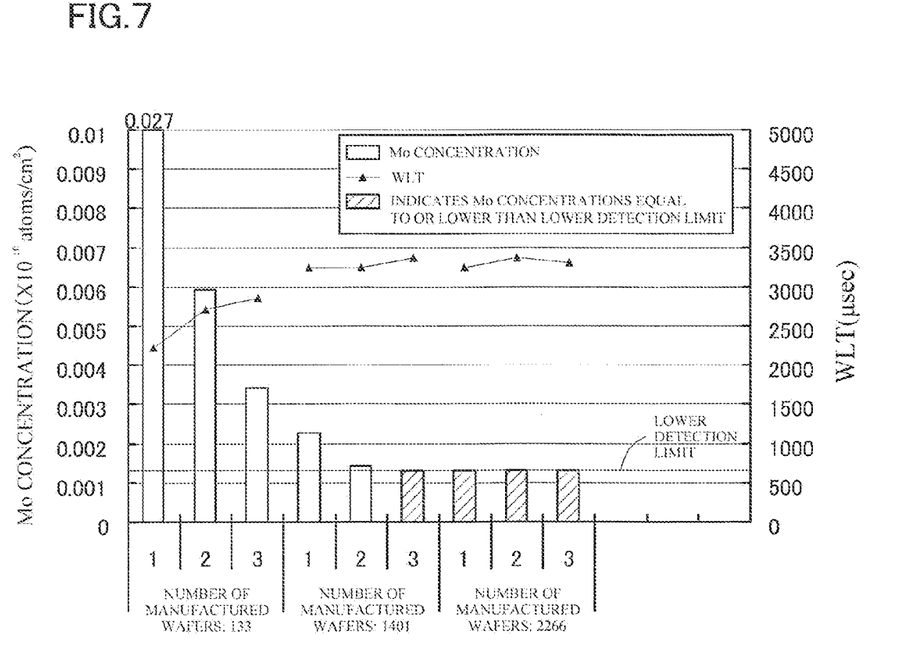
FIG. 7 is a diagram showing Mo concentrations and WLTs obtained when the number of epitaxial wafers to be produced after maintenance of a vapor phase growth apparatus is varied, as a result of measurement according to Example 3.

After maintenance of a vapor phase growth apparatus, the same VE and annealing as those of Example 1 were performed four times and comparison of Mo concentrations was performed, at a time when 133 silicon epitaxial wafers having a diameter of 300 mm had been manufactured, at a time when 1401 silicon epitaxial wafers had been manufactured, and at a time when 2266 silicon epitaxial wafers had been manufactured. FIG. 7 shows the result of the measurement. FIG. 7 also shows the resultant WLTs. As shown in FIG. 7, the lesser the number of wafers manufactured after the maintenance is, the higher the Mo concentration is in order of the first wafer, the second wafer, and the third wafer. The difference in the Mo concentrations is more prominent as compared to the difference in the WLTs. However, after 2266 wafers had been manufactured, contamination due to the maintenance seemed to be removed by evacuation or the like, and FIG. 7 shows that the Mo concentrations of the first to third wafers are equal to or lower than the lower detection limit. Thus, in the invention, it is easy to judge recovery of contamination after maintenance.

The invention is not limited to the above embodiment, and various modifications are possible without departing from the description of the scope of the appended claims. For example, the vapor phase growth apparatus to be subjected to measurement of the amount of contamination is not limited to a single-wafer-processing type. The invention is applicable to measurement of the amount of contamination of various types of vapor phase growth apparatuses such as a vertical type (pancake type), a barrel type (cylinder type)

and the like. Further, in the step S5 shown in FIG. 2, instead of the Mo concentration, the concentration of another metal impurity having a low diffusion rate, such as Sn, W, Ta, Ti, Al or V, maybe measured. Further, in the step S5, the Mo concentration may be measured by using a wafer surface analysis method other than ICP-MS, such as Total Reflection X-Ray Fluorescence (TXRF). Further, in the step S3, a semiconductor wafer other than the silicon wafer may be subjected to annealing.

DESCRIPTION OF THE REFERENCE CHARACTERS 10 vapor phase growth apparatus
12 chamber

The invention claimed is:

1. A method of measuring an amount of contamination of a vapor phase growth apparatus, comprising:
   a vapor etching step of cleaning an inside of a chamber of a vapor phase growth apparatus by vapor etching using HCl gas;
   an annealing step of sequentially annealing a predetermined number of wafers, one by one, in a non-oxidizing atmosphere in the chamber after the vapor etching; and
   a measurement step of measuring a concentration of a metal impurity on a surface of each of the wafers annealed in the annealing step, as the amount of contamination of the vapor phase growth apparatus, wherein
   a process which performs the vapor etching step and performs the annealing step for the predetermined number of wafers after the vapor etching step is repeatedly performed a predetermined number of times,
   the annealing step is performed such that the same wafers are used throughout the repeated annealing step and the order of the wafers to be annealed is not changed throughout the repeated annealing step, and
   the measurement step is performed after the process has been repeatedly performed the predetermined number of times.

2. The method of measuring an amount of contamination of a vapor phase growth apparatus according to claim 1, wherein
   the non-oxidizing atmosphere is a hydrogen atmosphere.

3. The method of measuring an amount of contamination of a vapor phase growth apparatus according to claim 1, wherein
   the predetermined number of wafers is three or more wafers.

4. The method of measuring an amount of contamination of a vapor phase growth apparatus according to claim 1, wherein
   the predetermined number of times is four or more times.

5. The method of measuring an amount of contamination of a vapor phase growth apparatus according to claim 1, wherein
   the annealing is performed at 1000° C. to 1200° C. for 30 seconds or more.

6. The method of measuring an amount of contamination of a vapor phase growth apparatus according to claim 1, wherein
   in the measurement step, contamination on the surface of each wafer is collected, and the concentration of the metal impurity contained in the contamination is measured by ICP-MS.

7. The method of measuring an amount of contamination of a vapor phase growth apparatus according to claim 6, wherein
   a region from which the contamination is collected is an entire region of the surface of each wafer.

8. The method of measuring an amount of contamination of a vapor phase growth apparatus according to claim 6, wherein
   a region from which the contamination is collected is a part of the surface of each wafer.

9. The method of measuring an amount of contamination of a vapor phase growth apparatus according to claim 1, wherein
   in the measurement step, a concentration of Mo is measured as the concentration of the metal impurity.

10. The method of measuring an amount of contamination of a vapor phase growth apparatus according to claim 1, wherein
    a silicon wafer is used as the wafer.

11. A method of manufacturing an epitaxial wafer, comprising:
    adopting the method of measuring an amount of contamination of a vapor phase growth apparatus according to of claim 1; and
    vapor-phase growing an epitaxial film on a wafer by using a vapor phase growth apparatus in which contamination caused by a metal impurity is reduced to or below a certain level, based on a result of measurement performed by the method of measuring an amount of contamination.

12. The method of measuring an amount of contamination of a vapor phase growth apparatus according to claim 1, wherein:
    the non-oxidizing atmosphere is a hydrogen atmosphere; and
    the predetermined number of wafers is three or more wafers.

13. The method of measuring an amount of contamination of a vapor phase growth apparatus according to claim 1, further comprising:
    an evaluation step of evaluating a cause of metal contamination of the vapor phase growth apparatus, based on a relationship among the concentrations of a metal impurity of the predetermined number of wafers, which are measured by the measuring step.

* * * * *